United States Patent [19]

Hartman

[11] Plant 5,061

[45] Jun. 14, 1983

[54] CHRYSANTHEMUM PLANT

[76] Inventor: Fred Hartman, 867 Dickson St., Kirkwood, Mo. 63122

[21] Appl. No.: 316,393

[22] Filed: Oct. 29, 1981

[51] Int. Cl.[3] ..... A01H 5/00

[52] U.S. Cl. ..... Plt./79

[58] Field of Search ..... Plt./76, 79

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum selection known by the cultivar name Hartmann's Radiance. It is of the variety Dark Pinnacle, particularly distinguished by its standard, incurved form and its generally reddish bronze color throughout the petals, with little fading at maturity.

1 Drawing Figure

The present invention comprises a new and distinct cultivar of *Chrysanthemum morifoliium,* Ramat., hereinafter referred to by the cultivar name Hartmann's Radiance.

The new cultivar was observed by growing in a cultivated field of Kirkwood, Mo. as a mutation of the standard chrysanthemum Dark Pinnacle. The parent cultivar is disclosed in U.S. Plant Pat. No. 3,624 granted Sept. 24, 1974 to Grace Y. Nakano. The new cultivar was selected for its solid, generally reddish bronze color, as opposed to the pink flower color of the present cultivar. Asexual reproduction by vegetative cuttings taken by me at Kirkwood, Mo. has demonstrated that the characteristics of Hartmann's Radiance are firmly fixed and are retained through successive generations of asexual reproduction.

The parent cultivar Dark Pinnacle is, as noted, a cultivar having pink flower color, with such color being darker and more intense than Escapade, the parent cultivar of Dark Pinnacle. Except for the distinctive generally reddish brown flower color, the characteristics of Hartmann's Raddiance are essentially identical to the same characteristics of Dark Pinnacle, including fade resistance, even during hot weather.

The accompanying photographic drawing shows typical inflorescence of the new cultivar, with the colors being as true as possible with color illustrations of this type. Two flowers are shown, more completely to depict the shades of color at the center, the inside and reverse side of the petals, and general tonality from a distance. The photogrph was taken in July, thereby clearly illustrating the fade resistance of the cultivar in hot summer conditions.

Hartmann's Radiance has not been observed under all possible environmental conditions. The phenotype may vary significantly with variations in environment such as temperature, light intensity, and day length. The following observations, measurements and comparisons describe plants grown in Kirkwod, Mo. under greenhouse conditions which approximate those generally used in commercial practice. Color references are made to the R.H.S. Color Chart published by The Royal Horticultural Society of London, England.

THE PLANT

Origin: A mutation of Dark Pinnacle, disclosed in U.S. Plant Pat. No. 3,624.

Classification:

*Botanical.*—*Chrysanthemum morifolium,* Ramat., cv. Hartmann's Radiance.

Form: Perennial herbaceous upright bush.

Height: 36–40".

Growth: Vigorous, sturdy and upright.

Leaf:

*Size.*—16.2 cm. × 10 cm. (average).

*Shape.*—Ovate, deeply lobed.

*Texture.*—Smooth, finely pubescent.

*Ribs and veins.*—Prominent.

*Margin.*—Deeply lobed.

*Color.*—Yellow green 147/A.

The bud:

*Diameter.*—3.4 cm.

*Depth.*—2.5 cm.

THE FLOWER

Blooming period: Year-round with photoperiod control.

Response: Early, 8 weeks.

Flower type: Composite and incurved standard.

Borne: As a head of many florets on receptacle; naturally raceme; singly when disbudded.

Size: Very large when fully opened, with the diameter of the inflorescence being 13–14 cm.

Shape: Flat when bloom first opens, becoming more globular as bloom matures.

Petalage: Florets are numerous with capitulum arrangement.

*Form.*—Linear and incurved with obtuse apex.

*Texture.*—Soft.

*Color.*—The overall color of the florets at the center of the flower head at the swirl is 170B. As the florets mature the color of the upper petals is approximately 170C. The inside petal color ranges from 170A–B. The reverse side of the petals is 170C, with slight fading during maturation on the outside petals. General tonality from a distance is approximately 170C.

*Discoloration after full bloom.*—Fades very slightly, even in hot weather, a highly desirable commercial trait.

*Peduncle.*—Strength: Sturdy and upright.

*Persistence.*—Florets hang on and dry.

*Fragrance.*—Typical chrysanthemum.

Reproductive organs:

*Stamens.*—Numerous. Pollen: None visible.

*Pistils.*—Present.

I claim:

1. A new and distinct cultivar of chrysanthemum plant known by the cultivar name Hartmann's Radiance, as described and illustrated, and particularly characterized by its reddish bronze flower color and standard incurved form.

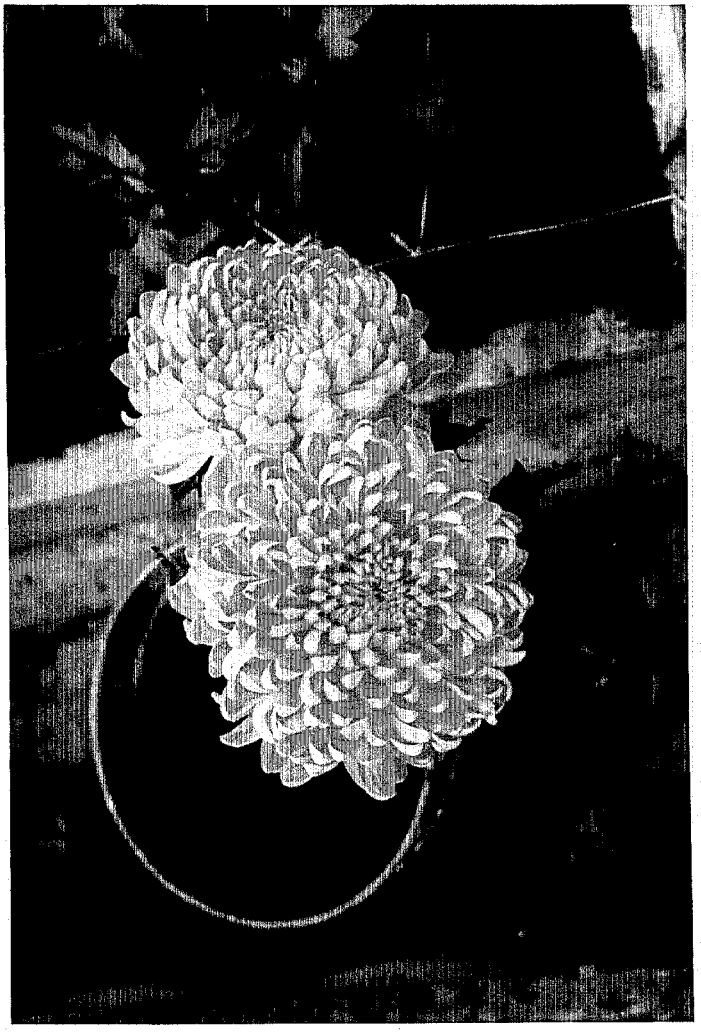

* * * * *